United States Patent [19]

Parslow et al.

[11] 4,298,494
[45] Nov. 3, 1981

[54] SHAMPOO

[75] Inventors: Michael W. Parslow, Upton by Chester; Stuart J. Sime, South Wirral, both of England

[73] Assignee: Lever Brothers Company, New York, N.Y.

[21] Appl. No.: 130,298

[22] Filed: Mar. 14, 1980

[30] Foreign Application Priority Data

Mar. 27, 1979 [GB] United Kingdom ............... 10636/79

[51] Int. Cl.$^3$ ........................... A61K 7/08; A61K 7/06
[52] U.S. Cl. ................................. 252/174.16; 252/550; 252/551; 252/557; 252/DIG. 13; 252/174.23; 424/70
[58] Field of Search ....... 252/550, 551, 557, DIG. 13, 252/174.16, 174.23; 424/70

[56] References Cited

U.S. PATENT DOCUMENTS 3,869,412  3/1975  Waag ......................... 252/174.16 X
4,061,602 12/1977  Oberstar et al. ............ 252/DIG. 13

Primary Examiner—Mayer Weinblatt
Attorney, Agent, or Firm—Melvin H. Kurtz

[57] ABSTRACT

The invention concerns an aqueous shampoo comprising an alkyl sulphate or alkyl ether sulphate detergent, a cationic derivative of a polygalactomannan gum as a hair conditioning agent and, for enhancing the deposition of the conditioning agent onto the hair during shampooing, a defined carboxylate, sulphate or phosphate ester anionic additive.

5 Claims, No Drawings

SHAMPOO

This invention relates to shampoos, and more especially to shampoos which contain a cationic derivative as a hair conditioning agent.

A number of cationic derivatives have been suggested for inclusion into aqueous liquid shampoos. Such derivatives are deposited upon the hair during the shampooing process and can impart useful hair conditioning benefits such as improved ease of combing. Generally speaking the benefit obtained is dependent upon the amount of the cationic compound left on the hair after the shampooing and rinsing procedures. The magnitude of the benefit obtained is therefore usually dependent on the amount of the polymer present in the shampoo.

Shampoo formulators have been concerned with devising ways of modifying shampoo formulae so as to increase the degree of deposition of the cationic hair conditioning agent so as either to enhance the conditioning effect or to be able to produce the same effect through the use of less of the conditioning agent. In German Patent Application No. 2 727 255 there is described the use of various inorganic salts for enhancing the deposition of the Polymer JR cationic resins from shampoos based on alkyl ether sulphate detergents.

Cationic polymeric materials which have more recently become of interest to shampoo formulators as potentially useful hair conditioning agents are cationic derivatives of polygalactomannan gums. These have been described in U.S. Pat. No. 3,589,978 and their use in certain shampoo formulae is disclosed in U.S. Pat. No. 4,061,602.

Of the detergents used in formulating shampoos the alkyl sulphate and alkyl ether sulphate anionic detergents are the most widely used. It is with the enhancement of the deposition of the cationic derivatives of polygalactomannan gums from such anionic-based shampoos that the present invention is concerned.

The present invention is based on our discovery that deposition onto the hair of a cationic polygalactomannan gum conditioning agent from a shampoo based on an alkyl sulphate or alkyl ether sulphate detergent is enhanced by including in the shampoo certain anionic additives.

Accordingly the present invention provides an aqueous shampoo comprising:

(A) from 5% to 30% by weight of an alkyl sulphate or alkyl ether sulphate detergent;

(B) from 0.05% to 2% by weight of a cationic derivative of a polygalactomannan gum; and (C) from 0.1% to 3% by weight of an anionic additive comprising at least one of (i) a carboxylate of the formula

R(OCH$_2$CH$_2$)$_n$COOM (ii) a sulphate of the formula

ROSO$_3$M (iii) a phosphate ester comprising a monoester of the formula

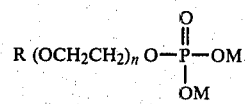

and/or a diester of the formula

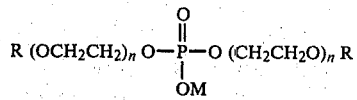

in which formulae R is a hydrocarbon group having 8 to 22 carbon atoms, n is 0 or an integer of from 1 to 10, and M is hydrogen or an alkali metal, ammonium or amine salt forming group, with the proviso that when the anionic additive component (C) is a sulphate the detergent component (A) is an alkyl ether sulphate. The group R may be an alkyl, alkenyl, cycloalkyl or cycloalkenyl group. Suitable amine salt forming groups constituting the group M include substituted ammonium groups, particularly the C1–C4 alkyl and hydroxy C1–C4 alkyl groups especially the mono-, di- and tri-ethyl, propyl, hydroxyethyl and hydroxypropyl-substituted ammonium groups.

The detergent employed in the shampoo of this invention is an alkyl sulphate or alkyl ether sulphate. Commonly used detergents of these kinds are the C10–C18 alkyl sulphates and C10–C18 alkyl ether sulphates containing 2 or 3 moles of ethylene oxide. These detergents are generally employed in the form of their sodium, potassium, ammonium or mono-, di- or tri-ethanolamine salts. Examples of these detergents are sodium lauryl sulphate, ammonium lauryl sulphate, mono-, di- and tri-ethanolammonium lauryl sulphates, sodium lauryl ether sulphate (2 EO), sodium lauryl ether sulphate (3 EO), potassium lauryl ether sulphate (2 EO), and ammonium lauryl ether sulphate (3 EO). The shampoo will generally contain from 8% to 25% by weight of anionic detergent.

The cationic hair conditioning ingredient is a derivative of a polygalactomannan gum. The gum occurs naturally as guar gum, the principal component of the seed of the guar plant, *Cyamopsis tetragonalobus*. The guar molecule is essentially a straight chain mannan branched at quite regular intervals with single membered galactose units on alternate mannose units. The mannose units are linked to each other by means of beta (1–4) glycosidic linkages. The galactose branching is accomplished through an alpha (1–6) linkage. The cationic derivatives are obtained by reaction between the hydroxyl groups of the polygalactomannan and reactive quaternary ammonium compounds. The degree of substitution of the cationic groups is desirably at least 0.01 and preferably at least 0.05, for example from 0.08 to 0.5. The quaternary ammonium compounds which can be used for preparing the cationic agents employed in this invention are those of the general formula

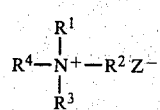

where R$^1$, R$^2$ and R$^3$ are methyl or ethyl groups and R$^4$ is an epoxyalkyl group of the formula

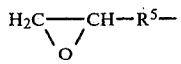

or halohydrin group of the formula

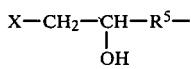

where $R^5$ is a C1–C3 alkylene group and X is chlorine or bromine, Z being an anion such as $Cl^-$, $Br^-$, $I^-$ or $HSO_4^-$.

An example of a suitable quaternary ammonium derivative is hydroxypropyltrimethylammonium guar gum of the formula

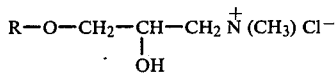

where R represents guar gum. Such a material is available commercially from Celanese-Stein Hall, USA under the name JAGUAR C-13-S; the word JAGUAR is a trade mark. This material also has the CTFA designation Guar Hydroxypropyltrimonium Chloride. In JAGUAR C-13-S the degree of substitution of the cationic group is about 0.13. Another suitable material is that known as JAGUAR C-17 which is similar to JAGUAR C-13-S but has a higher degree of substitution of cationic groups of about 0.25–0.31. A further example of a suitable guar derivative is the hydroxypropylated cationic guar derivative known as JAGUAR C-16 which as well as containing the above cationic quaternary ammonium groups also contains hydroxypropyl ($-CH_2CH(OH)CH_3$) substituent groups. In JAGUAR C-16 the degree of substitution of the cationic groups is 0.11–0.16 and the moles of substitution of hydroxypropyl groups is 0.8–1.1.

The cationic polygalactomannan gum derivative is present in the shampoo of the invention in an amount of from 0.05% to 2% based on the weight of the shampoo. Preferred amounts are from 0.1% to 1% by weight.

Examples of the carboxylate additive which may be present in the shampoo of this invention are sodium octanoate, sodium laurate, sodium stearate, sodium oleate and the corresponding potassium and ammonium and substituted ammonium compounds. Further examples are the ethoxylated fatty acids and salts thereof, such as oleic acid ethoxylated with six moles of ethylene oxide.

Typical examples of alkyl sulphates as the additive when the shampoo detergent is an alkyl ether sulphate are sodium lauryl sulphate and sodium stearyl sulphate. This specialised use of alkyl sulphates in small amounts to enhance deposition of a cationic polygalactomannan gum derivative must be contrasted with the use of larger amounts of these sulphates as the basic shampoo detergent.

The anionic phosphate ester additive of the shampoo according to the invention is usually produced commercially as a mixture comprising the mono- and di-esters defined above. They are available commercially under various trade names for example, BEROL, BRIPHOS and CRODAPHOS. BEROL 729 has alkyl chain lengths of 16–18 carbon atoms and contains series of 4 ethylene oxide units. In BRIPHOS L2D the alkyl chains are lauryl groups and it contains series of 2 ethylene oxide units. In BRIPHOS O3D and CRODAPHOS N3N the alkyl groups are oleyl and the ethylene oxide groups comprise 3 units. The weight ratio of mono-ester to di-ester may vary, typically from 1:10 to 10:1. Preferred phosphate esters are those in which n is 0 or an integer of from 1 to 6.

The anionic additive is included in the shampoo in an amount of 0.1% to 3% by weight of the shampoo, preferably from 0.2% to 2.5% by weight.

The shampoo of the invention may also include minor amounts of other ingredients which are commonly employed in shampoos, for example foam booster, thickener, opacifier, perfume, colouring agent, preservative, proteins, and an agent for adjusting pH, the latter usually being in the range 4 to 9 and is preferably from 5.5 to 7.5.

The shampoos of the invention may be prepared by dispersing the cationic polygalactomannan gum in water, then adding the detergent and the anionic additive. Any other ingredient may be incorporated along with the detergent and anionic additive, any adjustment of pH that may be desired conveniently being effected as the final step.

In the experiments reported hereinafter levels of deposition of the cationic guar gum derivative employed therein were compared using a dye uptake test. This test is based on the substantivity of a polyanionic direct azo dye to a cationic substrate. Hair on which cationic guar gum derivative has deposited will develop a red colour when in contact with the dye. The more cationic material deposited, the more intense the colouration of the hair by 66e dye.

DYE UPTAKE TEST

A 0.5 gm blond hair switch (about 10 cm long) was attached to a standard switch of hair (about 24 cm long, 10 gm) which acted as a carrier. The combined switch, after combing and wetting with water, was washed with the shampoo under test. This shampooing was done in two stages. In the first shampooing 0.5 ml of shampoo was applied to the wet hair, the switch lathered for 30 seconds and, after leaving for a further 20 seconds, rinsed with water. This was repeated but using 0.4 ml of shampoo, any tangles being combed from the switch whilst rinsing. After removing excess water, the switch was dried by hanging in a drying cabinet at 50° C. for one hour. The blond switch was removed and placed in the bottom of a 5 cm petri dish. 4 mls of a 0.1% aqueous solution of Pyrazol Fast Bordeaux 2BL adjusted to pH 3.5 with acetic acid were run into the dish from a burette and the hair probed with a spatula to ensure complete wetting of the hair by the dye solution. The switch was left in the solution for 30 minutes, rinsed with cold water and dried. At least two blond switches were treated in the above manner for each test product.

The invention will now be illustrated by reference to the following experiments. The experiments demonstrate the beneficial effect of carboxylate, sulphate and phosphate additives in enhancing deposition of cationic guar gum derivatives from shampoos in accordance with the invention. All percentages are by weight.

CARBOXYLATE ADDITIVE

Various shampoos were prepared having the following compositions:

|   | % | % |
|---|---|---|
| SLES (2 EO)[1] | 12.0 | — |
| SLES (3 EO)[2] | — | 12.0 |
| JAGUAR C-13-S | 0.3 | 0.3 |
| Sodium carboxylate | 0, 0.5, 1.0 | 0, 0.5, 1.0 |
| Water | to 100.0 | to 100.0 |
| pH adjusted to 6.5 | | |

[1]SLES (2 EO) is sodium lauryl ether sulphate containing 2 moles of ethylene oxide.
[2]SLES (3 EO) is sodium lauryl ether sulphate containing 3 moles of ethylene oxide.

These shampoos were made by dispersing the Jaguar C-13-S in cold water to form a 1% gel. To the required weight of the gel the surfactant, sodium carboxylate, if any, and the balance of the water were added and the mixture stirred. The pH was then adjusted with sodium hydroxide. Other shampoos described hereinafter were made in a corresponding manner.

Three different carboxylates were used, namely sodium octanoate, sodium laurate and sodium stearate.

By means of the dye uptake test it was shown that in every case the presence of the carboxylate increased the amount of the cationic gum deposited onto hair during shampooing.

Further shampoos containing a carboxylate that were employed in the dye uptake test were the following:

|   | % |
|---|---|
| SLES (2EO) | 12.0 |
| JAGUAR C-13-S | 0.1, 0.3 |
| CRODET 06[3] | 0, 1.0 |
| Water | to 100.0 |
| pH adjusted to 6.5 to 7.0 | |

[3]CRODET 06 is an ethoxylated oleic acid containing 6 moles of ethylene oxide.

The tests again showed that the presence of the carboxylate increased the amount of the cationic gum deposited onto the hair during shampooing.

In an experiment to investigate the effect of the presence of a carboxylate on the wet combing properties of the hair the following shampoos were compared:

| SLES (2 EO) | 12.0 | 12.0 | 12.0 | 12.0 |
|---|---|---|---|---|
| JAGUAR C-13-S | 0.1 | 0.1 | — | — |
| Sodium stearate | — | 0.5 | 0.5 | — |
| Water | to 100.0 | to 100.0 | to 100.0 | to 100.0 |
| pH adjusted to 6.5 | | | | |

Three hair switches (8 g each) were washed in a standard shampoo detergent solution (16% monoethanolamine lauryl sulphate) using the same method as previously described in the dye uptake test except that tangles were not combed out in the final rinsing stage. After removing excess water each switch was then combed through until free of tangles with a comb which was in association with an instrument which measured the total combing time. The same switches were then shampooed with the product under test using the same procedure. For each switch the combing time after treatment with the test product was expressed as a percentage of that after treatment with the standard shampoo. The average of the percentage values for the three switches was taken as the wet combing value for the test product. A different set of three switches was used for each test product. The wet combing values for the above four shampoos were, respectively, 69±7%, 55±1%, 134±81% and 152±33%.

The results showed that the presence of the carboxylate in the shampoo containing both resin and carboxylate additive led to an improvement in wet combing whereas the third shampoo containing only the carboxylate showed no improvement in wet combing properties over the detergent solution itself. This confirms that the improvement in wet combing is due to the increased deposition of the cationic resin brought about by inclusion in the shampoo of a carboxylate additive.

SULPHATE ADDITIVE

In the experiments involving the use of a sulphate additive the shampoos employed had the following compositions:

|   | % | % |
|---|---|---|
| SLES (2 EO) | 12.0 | — |
| SLES (3 EO) | — | 12.0 |
| JAGUAR C-13-S | 0.3 | 0.3 |
| Sodium alkyl sulphate | 0, 0.5, 1.0 | 0, 0.5, 1.0 |
| Water | to 100.0 | to 100.0 |
| pH adjusted to 6.5 | | |

The sulphates used in these tests were sodium lauryl sulphate and sodium stearyl sulphate.

By means of the dye uptake test it was shown that in all cases the presence of the sodium alkyl sulphate increases the amount of the cationic gum deposited onto the hair during shampooing.

PHOSPHATE ESTER ADDITIVE

Shampoos were made up according to the following composition:

|   | % |
|---|---|
| SLES (2 EO) | 12.0 |
| JAGUAR C-13-S | 0.3 |
| BRIPHOS 03D[4] | 0, 0.1, 0.2, 0.3, 0.4, 0.5, 0.6, 0.7 |
| Water | to 100.0 |
| pH adjusted to 6.5 | |

[4]BRIPHOS O3D is a mixture of approximately equal parts of mono- and di-phosphate esters of oleyl alcohol ethoxylated with three moles of ethylene oxide.

By means of the dye uptake test it was shown that at all the added levels of 0.1% to 0.7% the phosphate ester additive increases the amount of cationic gum deposited onto hair during shampooing.

In a separate test it was shown that phosphate ester itself does not lead to any uptake of dye in the dye uptake test.

Using the dye uptake test it was judged that the deposition of cationic resin from the above shampoo but containing 0.5% of the resin and no anionic additive was equivalent to that deposited from the shampoo containing 0.3% of resin and 0.5% of the phosphate ester. Similarly, the combination of 0.1% of the resin and 1.0% of the phosphate ester was found to be equivalent to 0.3% of the resin with no additive.

The following shampoos were employed in experiments to compare the wet combing properties of hair after shampoo treatment:

|  | % | % | % |
|---|---|---|---|
| SLES (2 EO) | 12.0 | 12.0 | 12.0 |
| JAGUAR C-13-S | 0.1 | 0.1 | 0.3 |
| BRIPHOS 03D | — | 1.0 | — |
| Water | to 100.0 | to 100.0 | to 100.0 |
| pH adjusted to 6.5 | | | |

In a manner similar to that described above, wet combing values were determined for each of the shampoos; these were, respectively, 69±7%, 48±15% and 48±8%. These results showed that the inclusion of the phosphate ester in the second shampoo improved the ease of combing compared with the first shampoo containing no phosphate ester. The test also indicated the equivalence in ease of wet combing of the second and third shampoos.

Other shampoos were made up having the following compositions:

|  | % | % |
|---|---|---|
| SLES (3 EO) | 12.0 | — |
| SLS[5] | — | 12.0 |
| JAGUAR C-13-S | 0.3 | 0.3 |
| BRIPHODS 03D | 0, 0.5, 1.0 | 0, 0.5, 1.0 |
| Water | to 100.0 | to 100.0 |
| pH adjusted to 6.5 | | |

5-SLS is sodium lauryl sulphate.

By means of the dye uptake test it was shown that in each case the added phosphate ester increases the amount of the cationic gum deposited onto hair during shampooing.

Further shampoos tested had the following compositions:

|  | % | % |
|---|---|---|
| SLES (2 EO) | 12.0 | — |
| SLES (3 EO) | — | 12.0 |
| JAGUAR C-13-S | 0.3 | 0.3 |
| BRIPHOS L2D[6] | 0, 0.5, 1.0 | 0, 0.5, 1.0 |
| Water | to 100.0 | to 100.0 |
| pH adjusted to 6.5 | | |

6-BRIPHOS L2D is a mixture of approximately equal parts of mono- and di-phosphate esters of lauryl alcohol ethoxylated with 2 moles of ethylene oxide.

By means of the dye uptake test it was shown that in all cases the added phosphate ester increases the amount of the cationic gum deposited onto hair during shampooing.

Further shampoos were made up having the following compositions:

|  | % | % | % |
|---|---|---|---|
| SLES (2 EO) | 12.0 | 12.0 | 12.0 |
| JAGUAR C-16 | 0.3 | — | — |
| JAGUAR C-17 | — | 0.3 | — |
| COSMEDIA GUAR C 261[7] | — | — | 0.3 |
| BRIPHOS 03D | 0, 0.5 | 0, 0.5 | 0, 0.5 |
| Water | to 100.0 | to 100.0 | to 100.0 |
| pH adjusted to 6.5-7.0 | | | |

7-COSMEDIA GUAR C261 is a cationic guar gum derivative available commercially from Henkel Corporation, USA; the word COSMEDIA is a trade mark.

By means of the dye uptake test it was shown that in each case the added phosphate ester increases the amount of the cationic gum deposited onto hair during shampooing.

Other specific examples of shampoos in accordance with this invention are given below:

|  | % |
|---|---|
| Example A | |
| SLES (2 EO) | 12.0 |
| JAGUAR C-13-S | 0.5 |
| BRIPHOS 03D | 2.5 |
| Water | to 100.0 |
| pH adjusted to 6.5 | |
| Example B | |
| Monoethanolamine lauryl sulphate | 20.0 |
| JAGUAR C-13-S | 0.3 |
| BRIPHOS 03D | 1.7 |
| Coconut diethanolamide | 5.0 |
| Water | to 100.0 |
| pH adjusted to 6.5 | |
| Example C | |
| SLS (3 EO) | 12.0 |
| JAGUAR C-13-S | 0.3 |
| BRIPHOS 03D | 1.0 |
| Water | to 100.0 |
| pH adjusted to 6.5 | |
| Example D | |
| SLES (2 EO) | 12.0 |
| JAGUAR C-13-S | 0.1 |
| BRIPHOS 03D | 1.0 |
| Water | to 100.0 |
| pH adjusted to 6.5 | |

What we claim is:
1. An aqueous shampoo consisting essentially of:
  (A) from 5% to 30% by weight of a detergent selected from alkyl sulphate and alkyl ether sulphate detergents;
  (B) from 0.05% to 2% by weight of a cationic derivative of a polygalactomannan gum; and
  (C) from 0.1% to 3% by weight of an anionic additive comprising at least one of
    (i) a carboxylate of the formula

$$R(OCH_2CH_2)_n COOM$$

(ii) a sulphate of the formula
    $$ROSO_3M$$

(iii) a phosphate ester selected from the group consisting of monoesters of the formula $$R(OCH_2CH_2)_n O-\overset{O}{\underset{OM}{\overset{\|}{P}}}-OM$$

and diesters of the formula $$R(OCH_2CH_2)_n O-\overset{O}{\underset{OM}{\overset{\|}{P}}}-O(CH_2CH_2O)_n R$$

and mixtures thereof
in which formulae R is a hydrocarbon group having 8 to 22 carbon atoms, n is 0 or an integer of from 1 to 10, and M is selected from the group consisting of hydrogen and alkali metal, ammonium and amine salt forming groups, with the proviso that when the anionic additive component (C) is a sulphate the detergent component (A) is an alkyl ether sulphate.

2. An aqueous shampoo as claimed in claim 1, wherein the detergent is a C10–C18 alkyl ether sulphate containing 2 to 3 moles of ethylene oxide.

3. An aqueous shampoo as claimed in claim 1, wherein the anionic additive is a phosphate ester.

4. An aqueous shampoo as claimed in claim 1, wherein the component (B) is a cationic guar gum derivative.

5. An aqueous shampoo consisting essentially of
 (A) from 5% to 30% by weight of a C10–C18 alkyl ether sulphate containing 2 to 3 moles of ethylene oxide;
 (B) from 0.05% to 2% by weight of a cationic guar gum derivative having a degree of substitution of cationic groups of from 0.01 to 0.5; and
 (C) from 0.1% to 3% by weight of a phosphate ester selected from the group consisting of monoesters of the formula

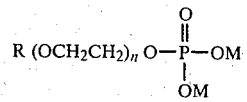

and diesters of the formula

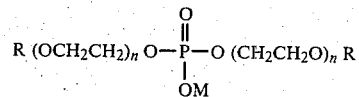

and mixtures thereof; and
 (D) water; in which formulae R is a hydrocarbon group having 8 to 22 carbon atoms selected from the group consisting of alkyl, alkenyl, cycloalkyl and cycloalkenyl groups, n is 0 or an integer of from 1 to 10, and M is selected from the group consisting of hydrogen and alkali metal, ammonium and amine salt forming groups.

* * * * *